United States Patent [19]
Wittenberger

[11] Patent Number: 4,599,176
[45] Date of Patent: Jul. 8, 1986

[54] PROCESS FOR THE PRODUCTION OF CELL STIMULATING AGENTS

[75] Inventor: Udo Wittenberger, Pratteln, Switzerland

[73] Assignee: Solco Basel AG, Basel, Switzerland

[21] Appl. No.: 495,956

[22] Filed: May 19, 1983

[30] Foreign Application Priority Data

May 21, 1982 [DE] Fed. Rep. of Germany ....... 3219248

[51] Int. Cl.$^4$ ............................................. B01D 13/00
[52] U.S. Cl. .................................. 210/639; 210/641; 210/651; 204/182.6
[58] Field of Search ............... 210/639, 641, 650, 651, 210/927; 204/180 P, 182.6; 424/101

[56] References Cited

U.S. PATENT DOCUMENTS

| | | | |
|---|---|---|---|
| 3,746,591 | 7/1973 | Banfield | 210/321.1 X |
| 3,972,614 | 8/1976 | Johansen et al. | 356/36 |
| 3,973,001 | 8/1976 | Jaeger et al. | 424/177 X |
| 4,013,791 | 3/1977 | Wissmann et al. | 424/177 |
| 4,166,948 | 9/1978 | Mittenzwei et al. | 55/67 X |
| 4,322,275 | 3/1982 | Jain | 210/927 X |
| 4,350,581 | 9/1981 | Schmoldt et al. | 204/301 |

FOREIGN PATENT DOCUMENTS

| | | |
|---|---|---|
| 1076888 | 3/1960 | Fed. Rep. of Germany . |
| 2065812 | 1/1976 | Fed. Rep. of Germany . |
| 2512936 | 9/1976 | Fed. Rep. of Germany . |
| 2946284 | 5/1981 | Fed. Rep. of Germany . |

OTHER PUBLICATIONS

Porter, M. C. et al, "Membrane Ultrafiltration", Chem. Tech., Jan. 1971, pp. 56–63.

*Primary Examiner*—David Sadowski
*Attorney, Agent, or Firm*—Bert J. Lewen; Henry Sternberg

[57] ABSTRACT

The invention concerns a process for obtaining cell respiratory stimulating active agents having a molecular weight in the range of about 300 to 8000 Dalton, by defibrination of calves blood, hemolyzing the solution obtained thereby, separating the proteins and substances having a molecular weight of over about 8000 Dalton comprised in the hemolyzed solution by a membrane separation procedure, concentrating the resulting protein- and high molecular weight-freed solution under reduced pressure at a temperature not exceeding 40° C. to a density in the range of 1.10 to 1.15 g/ml at 20° C. and partially separating the inorganic salts from the resulting concentrated solution, wherein the membrane separation procedure employed is a continuous multi-step ultrafiltration procedure employing membranes with a molecular weight exclusion limit of about over 8000 Dalton and the partial separation of the inorganic salts is carried out by electrodialysis with the aid of membranes with a membrane permeability up to a molecular weight of about 300 Dalton.

17 Claims, 2 Drawing Figures

PROCESS FOR THE PRODUCTION OF CELL STIMULATING AGENTS

BACKGROUND OF THE INVENTION

This invention relates to a process for the production of cell stimulating agents. More particularly, the invention relates to a process for obtaining a solution of cell respiration stimulating active agents from calves blood.

It is known from German Pat. No. 10 76 888 that one can obtain cell respiration stimulating active agents from bovine blood. In the process there described, one for example defibrinates fresh calve's blood, subjects the solution obtained to hemolyses, separates off the higher molecular weight components from the hemolysed solution obtained, such as in particular proteins, carries out a dialysis procedure and directly obtains a solution of active agent suitable for therapeutic uses by carrying out a subsequent mild concentration to a dry substance weight of 30 to 60 mg/ml. The dialysis required in this procedure can be carried out with any well known and conventional dialysis material to achieve the objects therein stated, whereby the use of cellophane tubes are indicated to be particularly suitable.

Although the above procedure does lead to a product with the desired therapeutic activity, it however possesses the disadvantage that the dialysis required is comparatively time-consuming and difficult to perform. Also, the product obtained is not the same uniform product since the upper molecular weight limit and accordingly its composition are subject to variations. Furthermore the yield of product obtained leaves much to be desired.

The process of the German Pat. No. 10 76 888 furthermore also leads to a product with a relatively high content of inorganic salts, in particular sodium chloride and potassium chloride. Such salts can not be separated off by the procedure therein described. The salt content of active agent solutions obtained can for example make up about 25 to 80% by weight of the solids content, so that corresponding injectable solutions or high concentration topical forms are several times hypertonic. As a result of this hypertonicity, intramuscular administration of such active agent solutions is on the one hand accompanied by pain and on the other hand by cell damage, which is disadvantageous to the desired cell regeneration effect.

The undesirable excessively high salt content of cell respiratory stimulating agents obtained by the procedure of the German Pat. No. 10 76 888 could in principle be lowered by several different methods, so that an isotonic or only slightly hypertonic solution of active agent is thereby obtained, namely for example by dialysis, ultrafiltration, ion-exchange or gel-filtration. All of these procedures are either not at all useable or are only useable with very unsatisfactory results. In accordance with German Pat. No. 25 12 936, the problem of desalting or partial desalting of the cell respiration stimulating active agent solution under discussion, should be solved by employing a very special gel-filtration procedure, namely by bringing the strongly salt-containing solution of the cell respiratory stimulating active agents into contact with a filtration layer situated on a perforated centrifuge drum and consisting of a gel with a high degree of cross-linking at a proportion of solution to gel volume of about 1:2.5 to 1.4.5. In this German Patent there are also at the same time described in detail the disadvantages of the other known procedures which are in principle possible for obtaining a partial desalting. All of these possible process procedures, including the process described in German Pat. No. 25 12 936, however, possess the disadvantage that their separation efficiency is very low and the apparatus required is very large, since as a rule these procedures have to be carried out at high dilutions. Furthermore, they are accompanied by higher or lower losses of active agent, since additional to the desired separation off of the inorganic salts, an adsorption of the cell respiration stimulating active agents on the separating medium also takes place. The essential regeneration of the gels and ion-exchange resin which is thereby necessary also requires a great amount of time and enables only a discontinuous working procedure with continuous change of the separating conditions.

The process for obtaining cell respiration stimulating active agents known from German Pat. No. 10 76 888, as a result of above, possesses the most differing disadvantages, and these could also not be solved by the additional considerations of the process described in German Pat. No. 25 12 936 for separating the excessively high content of disadvantageous inorganic salts.

It is therefore an object of the present invention to provide a new process for obtaining cell respiration stimulating active agents of the nature under discussion, which does not possess the disadvantages of the known working procedures and which can in particular be carried out simply and continuously, which is controllable in clean-cut fashion so that a product is obtained with a consistent upper—and to an extent also lower—molecular weight limit and further which leads directly to a solution of the cell respiration stimulating active agents by the provision of a controlled partial desalting procedure.

SUMMARY OF THE INVENTION

The process in accordance with the invention for obtaining a solution of cell respiration stimulating active agents from calves blood, comprises the step of defibrinating fresh calves blood, hemolysing the defibrinated calves blood, subjecting the hemolysed calves blood to a membrane ultrafiltration procedure with the aid of an ultrafitration membrane having a molecular weight exclusion limit of about over 8000 Dalton, collecting the ultrafiltrate solution comprising respiration stimulating active agents having a molecular weight of below about 8000 Dalton, and subjecting the collected ultrafiltrate solution to an electrodialysis procedure with the aid of electrodialysis membranes having a permeability up to a molecular weight of about 300 Dalton, whereby inorganic salts and other ionic lower molecular weight substances are partially separated out from the solution of cell respiration stimulating active agents.

The process in accordance with the invention leads to a therapeutic product in which the cell respiration stimulating activity is essentially the same as the products obtained in accordance with German Pat. No. 10 76 888, but provides through the employment of the combination of ultrafiltration and electrodialysis a significant improvement in a number of respects. The ultrafiltration provides a uniform product with a clean-cut separation of the proteins and other high molecular weight substances, with the simultaneous advantage of an improved economy regarding time required, space required and yield. The fact that one can employ the solution obtained by the ultrafiltration after a certain reduction in volume followed by electrodialysis, possesses the advantage that on the one hand one can employ a relatively concentrated solution, for example a solution with a solids content of 15 to 30% by weight, and that one can thereby work in a practically stationary equilibrium which sets in after an initial phase on the ion-exchange membranes. By changing the parameters of current density, temperature and time, it is furthermose possible to control the desalting procedure in determined directions and to so optimise that only a minimum of organic substance is lost. The degree of the particular desalting is most easily provided by a continuous measurement of the conductivity or also by a continuous determination of the osmolarity.

DETAILED DESCRIPTION OF THE INVENTION

Figure 1:
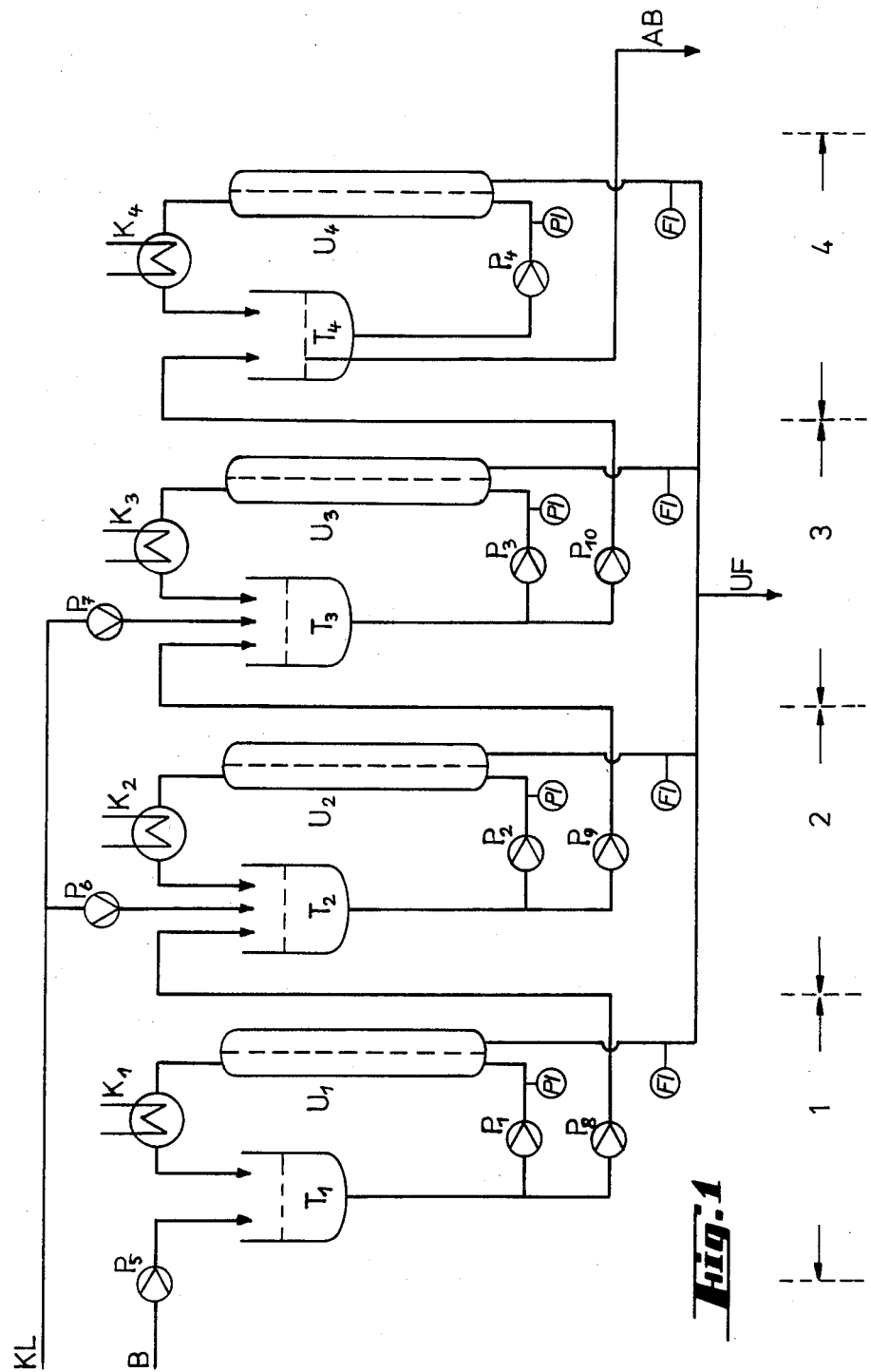
FIG. 1 shows an ultrafiltration apparatus which may be employed in the invention.

The known or inventive measures taken in the present process are otherwise carried out as follows:

The calves blood required as starting material is, immediately after having been taken, defibrinated by intensive stirring, if desired with cooling, and then filtering off the fibrin thus formed. The step is normally carried out directly in the particular abbatoirs.

After completion of the defibrination, the blood, if desired after mixture with a conservation agent, is immediately frozen and stored in frozen condition until required for further use.

In order to liberate the cell respiration stimulating active agents, it is necessary to subject the defibrinated blood or blood frozen for storage to a hemolysis, namely a break down of the red blood cells. For this purpose the cell membranes of the blood particles must be ruptured in some or other fashion.

Such rupturing can be achieved by both chemical and mechanical methods. For chemical hemolysis, one treats the defibrinated blood for example with ferments or bacteria, which attack and rupture the cell membranes. The mechanical hemolyses can take place either by addition of agents which lead to an elevation of the osmotic pressure within the cells, for example by the addition of water or organic solvents such as ethanol, diethyl ether or acetone, whereby the cell membranes then burst, or hemolysis can be obtained by the socalled ice-hemolysis, in which the blood is slowly cooled in such a fashion that larger ice crystals can develop which penetrate the cell membranes. After the hemolysis, practically all red blood cells are ruptured and the substances contained therein are set free.

The hemolysis is conveniently also carried out in the presence of a conservation agent.

The blood obtained hereby is then ready for carrying out the first step in accordance with the invention of the present process, namely, ultrafiltration employing membranes having a molecular weight cut-off limit of over about 8000 Dalton, and preferably over about 5000 Dalton.

The membranes employed in the ultrafiltration can consist of the most different materials, whereby membranes of cellulose triacetate or hydrophylic polyolefine are preferred.

Membranes of the above nature with a molecular weight cut-off limit of 8000 Dalton are characterised by their permeability, which is 100% separation of dextran with a molecular weight of 20,000, a nominal 85% separation of dextran with a molecular weight of 10,000, a nominal 50% separation of polyethyleneglycol with a molecular weight of 6000 and a nominal 10% separation of lactose with a molecular weight of 342.

Membranes with a molecular weight cut-off limit of over about 5000 Dalton are in respect of their permeability characterised by a 100% separation of dextran with a molecular weight of 10000, a nominal 97% separation of polyethyleneglycol with a molecular weight of 6000 and a nominal 30% separation of polyethyleneglycol with a molecular weight of 1000.

The solution obtained by ultrafiltration of calves blood after defibrination and hemolysing with employment of the membranes of the nature described, provides a finished product with an upper molecular weight limit of about 8000 Dalton or of about 5000 Dalton.

For carrying out a continuous multiple-step ultrafiltration, an ultrafiltration apparatus consisting of four units is advantageously employed, as is described in greater detail in the Example in conjunction with FIG. 1. Such an apparatus comprises ultrafiltration modules with type designation B 1, as is described in more detail in the brochure BPL 3/73 2M of the firm Paterson Candy International Ltd., Reverse Osmosis Division, Whitchurch, Great Britain and which is also described in German Patent Application No. 20 65 812. This special apparatus comprises membranes with a molecular weight cut-off limit of over about 8000 Dalton. It can however equally well be fitted with membranes with another molecular weight cut-off limit, for example a molecular weight cut-off limit of over about 5000 Dalton.

The ultrafiltration apparatus is operated with the use of pressures of for example 8 to 10 bar and cooling of the solution to be ultrafiltered to a temperature of for example 18° to 22° C. It is advantageously supplied with a solution of calves blood which has been conserved with a conventional conservation agent, for example an alcoholic solution of 4-hydroxy-benzoic acid methyl ester or 4-hydroxy-benzoic acid propyl ester, whereby an ethanolic solution of a combination of these two conservation agents is preferred.

Between the first step and the last step of the continuous multiple step ultrafiltration as diluent for the concentrated and then again to be ultrafiltered blood solution advantageously such an amount of a conservation agent solution is added that the drained off amount of ultrafiltrate is compensated by maintaining an about constant level of blood solution to be ultrafiltered again in the next step. Advantageously all steps but the last step of the continuous multiple step ultrafiltration are conducted while maintaining a near constant level of blood in the solution to be ultrafiltered. Only in the last step preferably no dilution of the blood solution coming from the last but one step is made so that here the blood load is totally dialysed under reduction of volume.

The waste blood resulting eventually from the ultrafiltration is discarded.

The ultrafiltrate obtained from the ultrafiltration, freed of proteins and higher molecular weight substances is subjected to a further step of volume reduction under reduced pressure at a temperature of not more than 40° C. The solution is reduced in volume to a density in the range of 1.10 to 1.15 g/ml at 20° C., for example by distillation under reduced pressure at a temperature of for example 30 to 35° C. The purpose of this concentration is firstly to remove the organic solvents which were optionally employed for hemolysis or for the organic solvent required for the specific conservation agent with simultaneous removal of the conservation agent, and secondly a concentration of the ultrafiltered solution to a dry content, namely for example a dry content of 180 to 230 mg/ml, suitable for carrying out the subsequent electrodialysis step of the invention. The precipitated conservation agent resulting from this concentration is best separated off by filtration, whereby residual conservation agent, if any, in the solution can be precipitated by suitable adjustment of the pH-value of the solution, for example, by addition of small amounts of concentrated hydrochloric acid up to a pH-value of 5, and then filtered off. The distillation required for this concentration is conveniently carried out in a suitable vacuum evaporator.

The concentrate obtained by the above concentration is then subjected to the second of the process steps of the invention, namely, the step of electrodialysis with the aid of a cell stack of alternatively arranged cation - and anion-exchange membranes with a membrane permeability up to a molecular weight of about 300 Dalton and preferably up to a molecular weight of about 400 Dalton, for partially separating off the inorganic salts therein contained and for forming an isotonic to slightly hypertonic solution having an osmolarity in the range of 250 to 550 mOsmol or a conductivity in the range of 40 to 75 mS/cm or a density at 20° C. in the range of 1.05 to 1.08 g/ml.

The membranes employed for this purpose are characterised by a permeability for inorganic or organic ions having a molecular weight up to about 300 or preferably up to about 400, whilst these membranes are closed to oligopeptides and larger molecules.

With the employment of such membranes, a lower molecular weight permeability limit of about 300 Dalton or preferably of about 400 Dalton is provided for the active agents.

The electrodialysis can be carried out under conditions which are conventional for separating inorganic salts from corresponding aqueous concentrates, so that the step of the invention here may for example work with a current density range of 5 to 70 mA/cm$^2$ free membrane cross-section, preferably 20 to 50 mA/cm$^2$ free membrane cross-section, a direct current voltage of 0.2 to 2 V per membrane pair, preferably 0.5 to 1 V per membrane pair, and a temperature range of 5° to 30° C.

The above step of electrodialysis can be carried out by employing conventional electrodialysis apparatus of a cell stack of alternately arranged cation- and anion-exchange membranes with the specifically desired permeability. In the example, an electrodialysis apparatus is employed which is in accordance with FIG. 2, which is later described in more detail. This is an apparatus of type designation BEL 2 from Berghof GmbH, Tübingen, Germany. The membranes of this apparatus reflect a membrane permeability up to a molecular weight of about 400 Dalton. A detailed description of the cell stack of this electrodialysis apparatus is shown in published German Patent Application No. 29 46 284.

The aqueous solution with a content of cell respiration stimulating active agents obtained in accordance with the process of the invention may, dependent on the intended form of application, either be employed directly for therapeutic uses, or if desired diluted further with pyrogen-free water or where required further concentrated. The corresponding pharmaceutical form may thus for example be solutions, aerosols, pastes, creams or gels. The cell respiration stimulating activity is, as already mentioned, essentially the same as for the substances obtained by German Pat. No. 10 76 888. Accordingly such medical forms are especially used for the promotion and control of healing processes. The dosage of active agent employed for this purpose is dependent on the mode administration as well as the nature and the seriousness of the condition being treated. Types of wounds which may be treated with the cell respiration stimulating active agents obtained by the present process are for example burns, ulcers or decubitus. For this purpose, the active agent can be administered intravenously, intraarterially, intramuscularly, or in the case of open wounds, also topically. In an injection therapy, such as in the treatment of ulcers in human subjects, an intravenous or intraarterial daily dose of 200 to 800 mg of active agent is for example required, and thereafter a follow-up treatment by intravenous or intramuscular administration of daily doses of 80 to 200 mg active agent.

Concerning this and other possible uses of such an active agent, reference is made in general to the brochure "Solcoseryl reaktiviert den gestörten Energiestoffwechsel der Zelle, regeneriert das Gewebe" of Solco Basel AG, Birsfelden, Switzerland, with the Publication no. SS-CH/d-6.81.

An important requirement for the successful employment of the process of the invention is that the biological activity of the calves blood extract is not influenced, and this particularly in the ultrafiltration and more particularly in the electrodialysis. In accordance therewith the original biological activity must be fully maintained. According to the process of the invention, a blood extract should be obtained which corresponds at least to the biological activity of product obtained by the German Pat. No. 10 76 888 or which is even higher.

The danger of a possible loss in biological activity during the ultrafiltration to be performed in accordance with the invention may be regarded as small, since in this step of the process only proteins and higher molecular weight substances are separated off and the major proportion of the biological activity determined by corresponding experiments should reside in the lower molecular weight range of the cell respiration stimulating active agents recoverable by the present process. It can also be taken that the ultrafiltration will not lead to any additional influence on the blood extract than the simple dialysis to be performed according to the process of German Pat. No. 10 76 888. A comparative test on the possible influence on the biological activity by the ultrafiltration of the invention is thus not necessary.

Similarly, the concentration of the solution following the ultrafiltration is also carried out under conditions which can not be associated with any influence on the biological activity of this blood extract. Thus, with this step also, comparative tests are not necessary.

On the other hand, the separation of inorganic salts comprised in the active agent concentrate by electrodialysis could lead to a negative influence on the biological activity of the blood extract. Here, relatively high amounts of salts must be separated off, and the molecular weights of the salts to be separated are comparatively close to the lower molecular weight limit of the cell respiration stimulating active agents to be obtained in accordance with the invention. It is therefore necessary to determine with the aid of suitable experiments whether the biological activity of the active agent solution obtained by electrodialysis, as compared to the starting material concentrate, has been influenced. Also, it is of course to be determined how the physical characteristics are influenced by this electrodialysis as compared to the starting material concentrate and which important substances additional to the inorganic salts are removed.

The comparative experiments related to the particular level of biological activity are performed by three different methods, namely by (a) Testing of the growth-stimulating activity on fibroblasts after damaging by carbonate withdrawal (Providing of the fibroblast activity), (b) Testing of the $O_2$-metabolism increasing activity according to Warburg (Providing the Warburg activity) and (c) Testing the wound healing promoting activity with standardized, dorsal burn wounds on rats (Providing the wound healing time against physiological saline)

The first two in vitro tests reflected that the full biological activity is retained under all test conditions and even improved in part, since the cell damaging salts are no longer present. The wound healing experiments provided the expected results that the partially desalted blood extracts obtained by the present process are better tolerated.

In all of these comparisons, the activity of the non-desalted starting concentrate and the partially desalted extract are of course carried out under normalised conditions, that is with employment of solutions with the same content of organic active agent but not with the same dry content. For this purpose, the solutions to be compared are always diluted to a determined content of total nitrogen, for example to a nitrogen content of 1 mg/ml of injection solution, and this total nitrogen content is taken as representative of the available content of organic material in the particular solutions. Of course, one proceeds in precisely the same fashion also for solutions to be employed for therapeutic purposes, wherein each charge is additionally tested in the Warburg test and in the fibroblasts-test.

The changes in dry weight, conductivity, osmolarity and ash content are obtained with the aid of comparative tests. The changes between the starting concentrate and that obtained by separating off the low molecular weight substances, namely mainly the anionic ions and other low molecular weight products, are obtained by comparison of the chemical analyses for characteristic substances and parameters.

The results obtained in comparative experiments carried out with the aid of two different starting concentrates and eight partially desalted extracts obtained in accordance with the invention can be seen in Table I of the Example. They support that additional to the inorganic ions lower carbonic acids and amino acids are partially removed, the biological activity however being fully retained.

For the purpose of further supporting that the electrodialysis carried out in accordance with the invention does not lead to a change or only leads to an insignificant change in the composition of the blood extract as related to its organic components, high pressure liquid chromatographic experiments were carried out. Here, the chromatograms obtained were each time identical for the starting concentrate and the partially desalted extracts.

The process of the invention is further illustrated by the following with the aid of an Example.

EXAMPLE

Ultrafiltration

An ultrafiltration apparatus of the nature mentioned in the introduction is employed (B1 from Paterson Candy International Ltd.). This four step ultrafiltration apparatus and its functioning can be seen schematically from FIG. 1.

Each step of the total four step apparatus (steps 1 to 4) is equipped with two ultrafiltration tube modules ($U_1$ to $U_4$) each having a 1.7 m$^2$ filter surface. Their membranes consist of cellulose acetate with the permeability characteristics already mentioned, namely a molecular weight permeability limit of over about 8000 Dalton. The pressure transfer pumps $P_1$ to $P_4$ are rotary piston pumps, which possess a capacity of about 1000 l/h at a pressure of 10 bars. The supply pumps $P_5$ to $P_7$ and the drain pumps $P_8$ to $P_{10}$ are dosage pumps, which can be freely adjusted within a range of 2 to 20 l/h. The total number of four tanks $T_1$ to $T_4$ each contain about 300 l. The added solutions are maintained at a temperature of 18° C. by coolers $K_1$ to $K_4$ cooled with cold water. PI in each case refers to pressure indicator devices, whereas FI refers in each case to flow indicator devices. The other abbreviations referred to therein have the following meanings:

B = defibrinated and hemolyzed blood solution
KL = Conservation agent solution
UF = ultrafiltrate
AB = waste blood To start the apparatus one supplies each of the tanks $T_1$ (step 1), $T_2$ (step 2) and $T_3$ (step 3) with each 250 l of defibrinated and hemolyzed calves blood B, which contains as conservation agent solution 15 volume percent of a 2% (weight/volume) alcoholic solution of a 9:1 mixture (weight/weight) of 4-hydroxybenzoic acid methyl ester and 4-hydroxybenzoic acid propyl ester. Then the pressure transfer pumps $P_1$ to $P_3$ are set in operation, whereby the ultrafiltrate UF begins to run out and the content of the tanks $T_1$ to $T_3$ reduces to the same degree. As soon as the content of the tanks $T_1$ to $T_3$ is about 150 l, the supply pumps $P_5$ to $P_7$ and the drain pumps $P_8$ to $P_{10}$ are set in operation. 10 l/h of conservation agent containing defibrinated and hemolyzed calves blood of the nature already described above are supplied over supply pump $P_5$. At the same time, 10 l/h of a conservation agent solution KL of 85 volume percent water and 15 volume percent of a 1% (weight/volume) alcoholic solution of a 9:1 mixture (weight/weight) of 4-hydroxybenzoic acid methyl ester and 4-hydroxy benzoic acid propyl ester is supplied to each of the tanks $T_2$ and $T_3$ over supply pumps $P_6$ and $P_7$. This leads to dilution of ultrafiltered loads. The drain pumps $P_8$ to $P_{10}$ are adjusted so that the level in the tanks $T_1$ to $T_3$ remains constant at 150 l.

In accordance therewith the tanks $T_2$ and $T_3$ are each supplied with such an amount of dilution agent KL that the amount of ultrafiltrate UF flowing from the individual ultrafiltration tube module $U_2$ and $U_3$ is compensated by maintaining a constant level of blood load. The same level of blood load is also maintained in tank $T_1$. Only in tank $T_4$ the level of blood load is lowered while carrying out the continuous multiple-step ultrafiltration by the amount of ultrafiltrate coming from ultrafiltration tube module $U_4$, because here no dilution agent is added in order to keep the level of blood load at about the same level as in the previous steps.

As soon as about 120 l of solution is available in tank $T_4$ (step 4) from the step 3, the pressure transfer pump $P_4$ is switched in. The waste blood passing out of the overflow of this tank $T_4$ is discarded.

After about 36 hours, an equilibrium has set in in all of the four steps. The ultrafiltrate UF flowing from the ultrafiltration tube modules $U_1$ to $U_4$ is thus representative of the present process, so that it may be collected for further use (subsequent concentration). The ultrafiltrate UF flow is about 4.7 l/h with step 1, about 11 l/h with step 2, about 10.4 l/h with step 3, and about 1.8 l/h with step 4. The amounts of ultrafiltrate UF transferred are accordingly 5.3 l/h for the drain pump $P_8$, 4.3 l/h for the drain pump $P_9$ and 3.9 l/h for the drain pump $P_{10}$, whilst the overflow of waste blood AB from the tank $T_4$ (step 4) is 2.1 l/h.

CONCENTRATION

The ultrafiltrate UF obtained by the above four stage ultrafiltration is then concentrated to a density of 1.130 mg/ml at 20° C. by distillation under reduced pressure of 30 mbar and a temperature of 35° C. and is hereby freed of the alcohol comprised in the conservation agent. With this concentration, most of the conservation agent also precipitates out, which is filtered off. The filtrate obtained is treated in small portions with concentrated hydrochloric acid until a pH value of 5 is reached, whereby the remaining amounts of conservation agent precipitates out. This precipitate is once again filtered off.

The material obtained by the above ultrafiltration and concentration is combined and serves as the starting concentrate with the designation 733.10 for the following step of electrodialysis in accordance with the invention.

Repetition of Ultrafiltration and Concentration

The above two process steps are repeated in every detail at a later point in time employing calves blood of a different origin, whereby one obtains a further starting concentrate with the designation 350.03 for the following step of electrodialysis.

Electrodialysis

Figure 2:
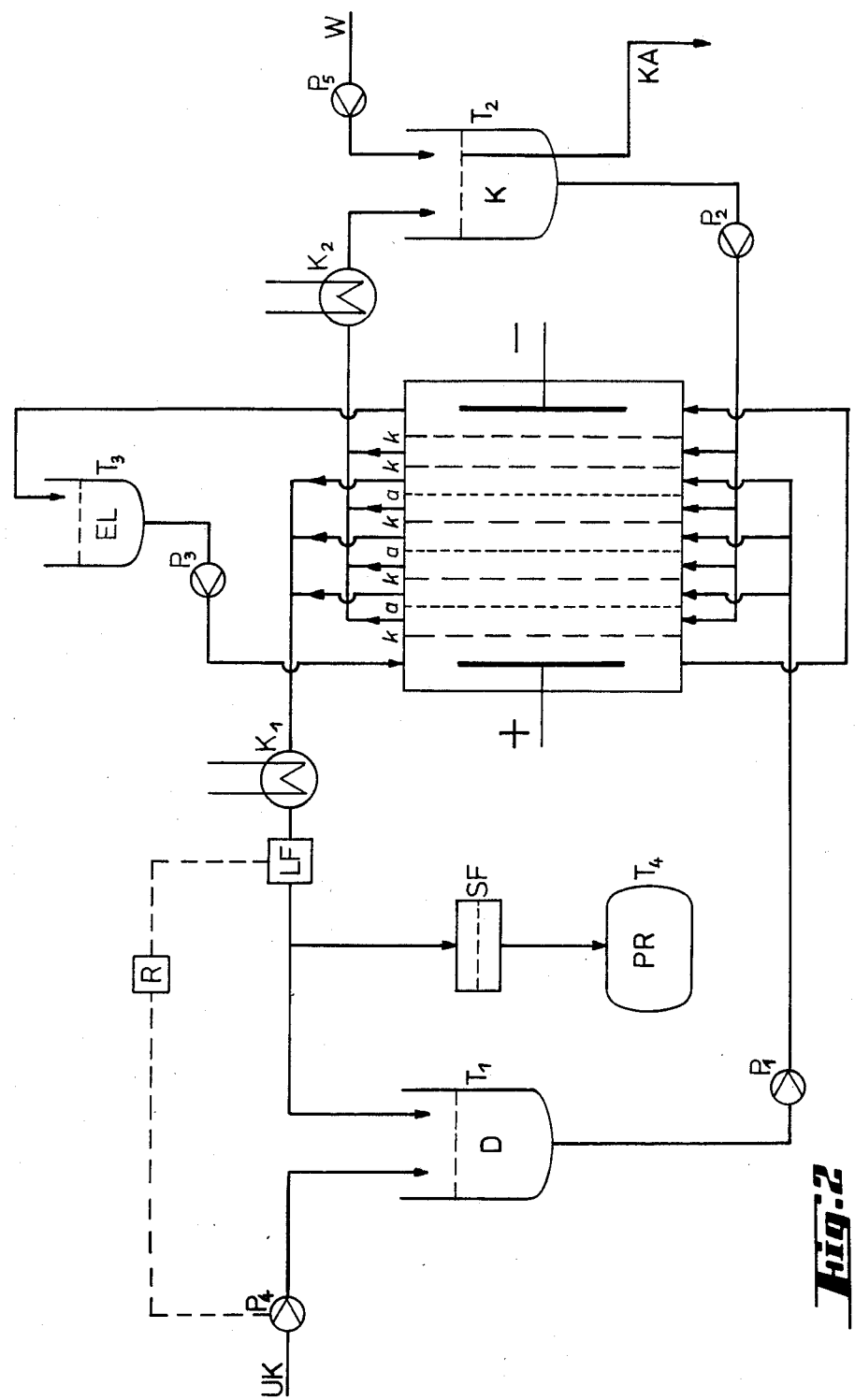
FIG. 2 shows an electrodialysis apparatus which may be employed in the invention.

The starting concentrates no. 733.10 and no. 350.03 obtained in the above fashion are once divided into two parts and the other time divided into six parts and are each added separately to the electrodialyses apparatus shown in FIG. 2. In this manner, one obtains the electrodialysates no. 12 and no. 13 with employment of the starting concentrate no. 733.10, and the electrodialysates No. 14, no. 15, no. 16, no. 17, no. 18 and no. 19 with employment of the starting concentrate 350.03.

An electrodialysis apparatus of the type mentioned in the introduction is employed (BEL 2 from Berghof GmbH). This apparatus and its function can be seen schematically from FIG. 2.

The central section of this apparatus is a cell stack which consist of seven pairs, each of an anion exchange membrane a and a cation exchange membrane k (Type CMV and AMV) and comprising on each side an additional membrane k as last membrane. (In the schematic drawing only three ion exchange membrane pairs are shown for simplicity reasons). The membranes employed have a permeability up to a molecular weight of about 400.

The following three liquid circuits are connected to the cell stack:

The solution to be desalted circulates from tank $T_1$ over a pump $P_1$ and a cooler $K_1$, which analogous to the literature is designated as diluate D.

An aqueous solution which takes up and enriches the salts, circulates from tank $T_2$ over a pump $P_2$ and a cooler $K_2$, and this solution is designated as concentrate K.

An aqueous solution of 2% sodium sulphate (weight/volume) circulates from tank $T_3$ over a pump $P_3$, and this solution is designated as electrode rinse solution EL.

The heat generated by friction is conducted away by the coolers $K_1$ and $K_2$ which maintain the solutions at 25° C.

A conductivity measuring cell LF is built into the diluate circuit D after the cooler $K_1$. The flow of concentrated down ultrafiltrate UK is regulated over a two-point regulator R.

A portion of the concentrated down salt solution KA is continuously carried away on the concentrate side and is replaced by distilled water W over the pump $P_5$. Additionally, a certain water transport takes place in the cell stack from the diluate side to the concentrate side.

A portion of the diluate D after measurement of the conductivity in the conductivity measuring cell is continuously withdrawn and after passing over a sterile filter SF is stored as finished product PR in tank $T_4$ at 0° C. until further working up into the corresponding finished pharmaceutical form.

To initiate operation of the electrodialysis apparatus, the 2 l-containing tank $T_1$ is added with 1.2 l of the concentrated ultrafiltrate UK produced in accordance with the procedure described above. 1 l of distilled water is added to the tank $T_2$ of the same size and 750 ml of a 2% $NaSO_4$ solution is added to the 1 l tank $T_3$. After the cell packet and all circuits are filled and freed of air, the three pumps $P_1$ to $P_3$ are set in operation, which each transport about 90 l/h. A direct current is applied to the two electrode plates (+ and −), whereby the voltage is so chosen that a current of about 20 mA/cm$^2$ flows on the free membrane cross-section. Thus, a total current of about 75 mA flows in the cell stack employed having a free membrane cross-section of 37 cm$^2$. The starting voltage of about 16 V is adjusted downwardly within 1 hour to a stationary value of about 5.5 V for the cell stack consisting of seven membrane pairs.

The conductivity has lowered to a value of between 45 and 50 mS/cm after 10 hours. The regulator R now regulates the supply of further concentrated ultrafiltrate UK over a dosage pump $P_4$ in such a fashion that the conductivity of the diluate remains between 45 and 50 mS/cm, in average at about 100 ml/h.

The dosage pump $P_5$ is set at 200 ml/h, and the outflow of the salt concentrate KA from the tank $T_2$ is about 220 ml/h.

The results obtained with the above dialysis several times repeated employing the two different starting concentrates no. 733.10 and no. 350.03 and formation of the different electrodialysates no. 12 and no. 13 as well as no. 14, no. 15, no. 16, no. 17, no. 18 and no. 19 are provided in the following Table I together with the applied conditions of temperature, current density and direct voltage as well as with the different analysis data for the starting concentrates and the recovered electrodialysates and the comparative data on the specific at least has the same or in part an even better biological activity than the corresponding active agent solution obtained by the known procedures.

|  | Dimension | | | | |
|---|---|---|---|---|---|
|  | Starting-concentrate No. 733.10 | Electro-dialysate No. 12 | Electro-dialysate No. 13 | Starting-concentrate No. 305.03 | Electro-dialysate No. 14 |
| Solids content mg/ml | 212,1 | 103,0 | 108,7 | 213,11 | 109,7 |
| Density (20° C.) g/ml | 1,129 | 1,057 | 1,060 | 1,129 | 1,060 |
| Conductivity mS/cm | 149 | 56 | 68 | 145 | 56 |
| Osmolarity mOsm | 1053** | 404*** | 497*** | 1052** | 414*** |
| Ash content % solids content | 66,25 | 33,90 | 41,80 | 75,57 | 34,55 |
| Total Nitrogen % solids content | 2,55 | 4,83 | 4,57 | 2,73 | 5,59 |
| Amino Nitrogen % solids content | 0,65 | 1,23 | 1,25 | 0,64 | 1,38 |
| Chloride % solids content | 35,88 | 15,74 | 19,31 | 37,17 | 12,28 |
| Sodium % solids content | 27,19 | 17,30 | 19,49 | 24,79 | 18,03 |
| Potassium % solids content | 4,34 | 1,59 | 2,14 | 3,78 | 1,20 |
| Glucose % solids content | 10,91 | 22,30 | 20,52 | 3,87 | 8,65 |
| Urea % solids content | 2,15 | 3,59 | 3,43 | 2,43 | 4,76 |
| Total Phosphorus % solids content | 0,78 | 1,52 | 1,39 | 0,77 | 1,75 |
| Lactate % solids content | 9,72 | 17,58 | 17,71 | 9,78 | 20,62 |
| Acetic Acid % solids content | 1,83 | 3,45 | 3,18 | 2,37 | 4,48 |
| Fibroblast-Activity Growth stimulation compared to Standard-Culture* | 1,6* °* | 1,5* *** | 1,5* *** | 2,0* ** | 1,1* *** |
| Warburg-Activity % compared to Standard | −2** | +10*** | +14*** | −6** | +5*** |
| Wound healing time against physiological Saline % Shortening | 9,9** |  | 13,7/10,9*** | 15,7** |  |
| Temperature °C. |  | 25 | 25 |  | 25 |
| Current density mA/cm³ |  | 50 | 50 |  | 50 |
| Direct current per membrane V |  | 0,7 | 1,0 |  | 1,0 |

|  | Dimension | | | | |
|---|---|---|---|---|---|
|  | Electro-dialysate No. 15 | Electro-dialysate No. 16 | Electro-dialysate No. 17 | Electro-dialysate No. 18 | Electro-dialysate No. 19 |
| Solids content mg/ml | 106,37 | 107,58 | 111,37 | 129,62 | 101,28 |
| Density (20° C.) g/ml | 1,057 | 1,058 | 1,060 | 1,073 | 1,052 |
| Conductivity mS/cm | 50 | 55 | 56 | 40(6° C.) | 46 |
| Osmolarity mOsm | 378*** | 410*** | 428*** | 510*** | 355*** |
| Ash content % SC | 32,48 | 36,11 | 36,72 | 43,90 | 28,10 |
| Total Nitrogen % SC | 6,26 | 5,61 | 5,87 | 5,13 | 6,16 |
| Amino Nitrogen % SC | 1,56 | 1,46 | 1,45 | 1,28 | 1,64 |
| Chloride % SC | 9,20 | 11,89 | 12,69 | 16,30 | 7,30 |
| Sodium % SC | 16,99 | 18,23 | 18,36 | 20,40 | 17,30 |
| Potassium % SC | 1,07 | 1,10 | 1,12 | 1,53 | 0,92 |
| Glucose % SC | 9,81 | 9,06 | 9,09 | 7,95 | 10,28 |
| Urea % SC | 5,39 | 4,56 | 5,11 | 4,34 | 5,04 |
| Total Phosphorus % SC | 1,91 | 1,75 | 1,67 | 1,56 | 1,94 |
| Lactate % SC | 22,72 | 21,29 | 21,63 | 18,32 | 22,60 |
| Acetic Acid % SC | 4,58 | 4,56 | 4,62 | 4,01 | 4,68 |
| Fibroblast growth stimulation compared to Standard-Culture* | 1,2* *** | 1,3* *** | 0,7* *** | 1,8* *** | 2,0* °** |
| Warburg-Activity % compared to Standard | +6*** | −7*** | +30*** | +9*** | +30*** |
| Wound healing time against physiological Saline % Shortening |  |  |  |  | 9,0*** |
| Temperature °C. | 25 | 25 | 25 | 6 | 25 |
| Current density mA/cm² | 50 | 22 | 50 | 50 | 20 |
| Direct current per membrane V | 1,2 | 0,8 | 1,2 | 1,3 | 0,4 |

SC = Solid Content
°All values over 1.0 are effective; quantitative lower graduations are no longer possible
**These data are based on an ultrafiltrate diluted by five times with sterile water
***These data are based on an electrodialysate diluted by five times with sterile water.

biological activity.

The concentrated diluate obtained by the above electrodialysis is advantageously diluted with sterile water—for example by five times—in order to form an isotonic to slightly hypertonic active agent solution having an osmolarity in the range of from 1 to 250 to 550 mOsmol.

The test results show that by employment of the process of the invention a cell respiration stimulating active agent solution can be prepared from calves blood in a particularly elegant and economical fashion, which

I claim:

1. A process for obtaining a solution of cell respiration stimulating active agents from calves blood, which comprises the steps of defibrinating fresh calves blood, hemolysing the defibrinated calves blood, subjecting the hemolysed calves blood to a membrane ultrafiltration procedure with an ultrafiltration membrane to separate an ultrafiltrate solution comprising a blood extract containing respiration stimulating active agents having a molecular weight of below 8000 Dalton from an ultrafiltered load, and subjecting said ultrafiltrate solution to an electrodialysis procedure at a current density of from 5 to 70 ma/cm$^2$, at a direct current of from 0.2–2 volts, and at a temperature of from 0° to 30° C. with electrodialysis membranes having a permeability up to a molecular weight of about 300 Dalton to partially separate out inorganic salts and aother ionic lower molecular weight substances from said ultrafiltrate solution without significantly changing the composition of the blood extract with respect to its organic components and to form a solution having a conductivity of from 40 to 75 mS/cm and a density at 20° C. of from 1.05 to 1.08 g/ml.

2. A process according to claim 1, in which the step of defibrinating fresh calves blood is carried out by intensive stirring of said calves blood and filtering off of fibrin thus formed.

3. A process according to claim 1, in which the step of hemolysing the defibrinated calves blood is carried out using ferments or bacteria which attack and rupture blood cell membranes.

4. A process according to claim 1, in which the step of hemolysing the defibrinated calves blood is carried out by adding thereto a substance which elevates osmotic pressure within calves blood cells, whereby blood cell membrances are ruptured.

5. A process according to claim 4, wherein the substrance added to the defibrinated calves blood is water, ethanol, diethyl ether or acetone.

6. A process according to claim 1, in which the step of hemolysing the defibrinated calves blood is carried out by slow freezing thereof whereby larger ice crystals develop which penetrate blood cell membranes.

7. A process according to claim 1, wherein said ultrafiltered load is diluted and subjected to the membrane ultrafiltration procedure again to obtain additional ultrafiltrate solution comprising cell respiration stimulating active agents.

8. A process according to claim 7, in which the steps of dilution of ultrafiltered load and membrane ultrafiltration are repeated.

9. A process according to claim 7, in which the membrane ultrafiltration procedure and the steps of dilution of ultrafiltered load and membrane ultrafiltration thereof are performed in a continuous fashion by means of a series of tanks for collecting ultrafiltered loads and diluent and a membrane ultrafiltration device downstream of each of the tanks.

10. A process according to claim 1, in which the membrane ultrafiltration procedure separates out an ultrafiltrate solution comprising a blood extract containing respiration stimulating active agents having a molecular weight of below 5000 Dalton.

11. A process according to claim 1, in which the steps of defibrination, hemolysis and ultrafiltration are carried out in the presence of a conservation agent for conserving the calves blood.

12. A process according to claim 11, in which the conservation agent is an alcohol solution of 4-hydroxy-benzoic acid methyl ester, 4-hydroxy-benzoic acid propyl ester, or a combination thereof.

13. A process according to claim 11, in which the conservation agent and any solvent therefor is eliminated from the ultrafiltrate comprising respiration stimulating active agents preliminary to carrying out the electrodialysis procedure.

14. A process according to claim 1, in which the ultrafiltrate solution comprising respiration stimulating active agents is concentrated down to a solids content of 180 to 230 mg/ml preliminary to carrying out the electrodialysis procedure.

15. A process according to claim 14, in which the concentration is effected by distillation under reduced pressure at a temperature not exceeding 40° C.

16. A process according to claim 14, in which the electrodialysis procedure is carried out on the concentrated ultrafiltrate solution by applying a direct current voltage of 0.5 to 1 V across anionic and cationic membrane pairs to achieve a current density within the range of 20 to 50 mA/cm$^2$ of free membrane area.

17. A process for obtaining a solution of cell respiration stimulating active agents from calves blood, which comprises the steps of defibrinating fresh calves blood, hemolysing the defibrinated calves blood, subjecting the hemolysed calves blood to a membrane ultrafiltration procedure with an ultrafiltration membrane to separate an ultrafiltrate solution comprising a blood extract containing respiration stimulating active agents having a molecular weight of below 8000 Dalton from an ultrafiltered load, and subjecting said ultrafiltrate solution to an electrodialysis procedure at a current density of from 5 to 70 ma/cm$^2$, at a direct current of from 0.2–2 volts, and at a temperature of from 0° to 30° C. with electrodialysis membranes having a permeability up to a molecular weight of about 400 Dalton to partially separate out inorganic salts and other ionic lower molecular weight substances from said ultrafiltrate solution without significantly changing the composition of the blood extract with respect to its organic components and to form a solution having a conductivity of from 40 to 75 mS/cm and a density at 20° C. of from 1.05 to 1.08 g/ml.

* * * * *